United States Patent [19]

Spanier

[11] Patent Number: 4,902,134
[45] Date of Patent: Feb. 20, 1990

[54] OPTICAL AMPLIFIER AND METHOD FOR AMPLIFYING OPTICAL POLARIZATION STATE CHANGE EFFECTS

[75] Inventor: Richard F. Spanier, Chester, N.J.

[73] Assignee: Rudolph Research Corporation, Flanders, N.J.

[21] Appl. No.: 152,005

[22] Filed: Feb. 3, 1988

[51] Int. Cl.[4] .............................................. G01J 4/00
[52] U.S. Cl. ..................................... 356/364; 356/367
[58] Field of Search .............. 356/364, 365, 366, 367, 356/368, 352, 33, 34, 35; 250/225

[56] References Cited

U.S. PATENT DOCUMENTS

| 3,537,080 | 10/1970 | Vorie et al. | 250/225 |
|---|---|---|---|
| 4,233,847 | 11/1980 | Walker | 356/33 |
| 4,305,046 | 12/1981 | Le Floch et al. | 356/350 |
| 4,498,774 | 2/1985 | Yeung et al. | 356/368 |
| 4,560,867 | 12/1985 | Papuchon et al. | 356/368 |
| 4,648,274 | 3/1987 | Trainer | 356/33 |

FOREIGN PATENT DOCUMENTS 2431140 8/1980 France .

OTHER PUBLICATIONS

Azzam, RMA "Measurement of the Jones Matrix of an Optical System by Return-path Null Ellipsometry", *Optica Acta* vol. 28, No. 6 pp. 795-800.

"Observation of an Amplified Optical Rotation" by Roger Stevens *Applied Optics,* vol. 26, No. 14, Jul. 15, 1987; pp. 2704–2705.

"Measurement of Small Rotations by Eigenvector Flips in a Quasi-Isotropic Fabry-Perot" by Y. Le Grand, et al., *Applied Physics Letters* 51(20) Nov. 16, 1987, pp. 1574–1576.

*Primary Examiner*—Richard A. Rosenberger
*Attorney, Agent, or Firm*—Antonelli, Terry & Wands

[57] ABSTRACT

An optical amplifier for amplifying optical polarization state change effects comprises an arrangement for passing polarized light through a material a plurality of times such that changes in the polarization state of the polarized light from the respective passes of the light through the material are cumulative. The amplifier can be used in a method for detecting optical polarization state change effects wherein polarized light which is passed through the material is detected. The material may be a liquid sample from a high performance liquid chromatography system.

23 Claims, 7 Drawing Sheets

OPTICAL AMPLIFIER AND METHOD FOR AMPLIFYING OPTICAL POLARIZATION STATE CHANGE EFFECTS

TECHNICAL FIELD

The present invention relates to an optical amplifier and method for amplifying optical polarization state change effects and, particularly, to a liquid chromatography system which employs the same.

BACKGROUND ART

The detection of optical polarization state change effects is well known. Such effects include optical rotation, circular dichroism, linear dichroism, optical activity, and Kerr effect. For example, optical rotation can be measured with a polarimeter for measuring concentration, purities and specific rotation which is a fundamental property of matter of certain compounds such as large organic molecules, pharmaceuticals, flavors, fragrances and sugar.

The limit of measurement of optical rotation by the best known apparatus today that are practical to build in quantity, is of the order of 0.0001° of measured rotation but the most practical apparatus has a sensitivity of only 0.001°. There are many applications where a more sensitive measurement capability is necessary or desirable, as in high pressure liquid chromatography and other applications where the concentration of the sample is very low or the materials constants are very low and where the concentration cannot be increased because of the limited volume of the sample available or in the analyzing of waste water where there is no control of the concentration. Waste water analysis can be used in various pharmaceutical plants to assure no contamination of waste water with optically active materials. In the sugar industry, boiler water analysis can be employed to determine if there are any leaks of the reactants or purification vessels that allow sugar solution into the heat exchangers and the cooling water.

One solution to the problem of detecting very small optical rotations has been suggested by Yeung et al. in U.S. Pat. No. 4,498,774. However, the apparatus disclosed therein, with present manufacturing limitations, is not practical to produce in quantity. Thus, there is a need for an improved apparatus and method for detecting very small optical polarization state change effects such as optical rotations of less than 0.0001°, which apparatus can be produced in quantity.

DISCLOSURE OF INVENTION

The present invention solves the aforementioned problems with the known apparatus and methods for detecting optical polarization state change effects by providing, according to the present invention, an optical amplifier and method for amplifying optical polarization state change effects so that very small optical polarization state change effects can be detected. This is accomplished according to the disclosed method by providing polarized light and passing at least a portion of the polarized light through a material a plurality of times such that changes in the polarization state of the polarized light from the respective passes of the light through the material are cumulative, and detecting the polarized light which is passed through the material. By increasing the path length of the polarized light through the material by passing the light through the material a plurality of times, a very small polarization state change effect can be amplified so that it can be detected.

The step of passing polarized light through a material a plurality of times comprises, according to the preferred mode of carrying out the method, reflecting light back and forth a plurality of times along an optic axis which extends through the material. Where polarized light is reflected back and forth through a material a plurality of times, the changes in the polarization state of the polarized light from the respective passes of the light through the material cancel each other. To prevent this, and to cause the changes in the polarization state of the polarized light from the respective passes of the light through the material to be cumulative, according to a further feature of the method of the invention, the step of passing polarized light through a material further comprises inverting the polarization state of the polarized light between passes through the material so that the changes in the polarization state in successive passes are cumulative. Where optical rotation is the optical polarization state change effect being detected, this permits optical rotations smaller than 0.0001°, and even smaller than 1 microdegree (0.000001°), to be detected with the apparatus and according to the method of the invention. A preferred use of the method is in detecting weak optical activity in an eluent in high performance liquid chromatography.

The optical amplifier of the invention for amplifying optical polarization state change effects comprises means for providing polarized light and means for passing at least a portion of the polarized light through a material a plurality of times such that changes in the polarization state of the polarized light from the respective passes of the light through the material are cumulative. According to the preferred form of the invention, the means for passing includes means for reflecting at least a portion of the polarized light back and forth a plurality of times along an optic axis of the amplifier which extends through the material. In order that the changes in the polarization state of the polarized light from the respective passes of the light through the material do not cancel each other, but are cumulative, the means for passing inverts the polarization state of the polarized light between passes through the material so that the changes in the polarization state in successive passes are cumulative. The means for inverting the polarization state includes a pair of quarter wave compensators which are provided in spaced relationship on the optic axis of the amplifier on opposite sides of the material between the material and the means for reflecting. The retardation of each quarter wave compensator must be maintained to a tolerance of 90°±1° and preferably is maintained to a high tolerance of 90°±0.3°. Each quarter wave compensator has two neutral lines. The neutral lines of each compensator are located at the same angles with respect to a direction of polarization of the polarized light from the means for providing polarized light.

The means for reflecting in the disclosed embodiment includes a pair of mirrors which are provided in spaced relationship on the optic axis on opposite sides of the material for reflecting at least a portion of the polarized light back and forth a plurality of times along the optic axis through the material. The mirrors each have a high reflectivity R of at least 0.9 and preferably at least 0.99.

The optical amplifier further comprises means for analyzing the polarization state of polarized light passed through the material. As disclosed, the means for analyzing polarized light comprises a polarizer. A photosensitive detector is also provided for detecting light intensity from the means for analyzing the polarization state of the polarized light passed through the material. Means for modulating the polarization state of the light which is received by the analyzing means can also be provided to aid in analyzing the output of the optical amplifier. The length of the path along the optic axis of the amplifier along which polarized light is reflected back and forth is also preferably selected to provide a resonance condition for the light. The advantage of this is that intensity of the polarized light emitted from the optical amplifier is significantly greater when the path length along the optic axis is adjusted for the resonance condition.

The present invention further includes a liquid chromatography system comprising a cell for containing a liquid chromatography sample and an apparatus for analyzing the sample in the cell for optical activity. The apparatus includes an optical amplifier of the invention for amplifying optical polarization state change effects, particularly, optical rotation. Using digital signal processing, or analog circuitry optical rotations of $10\mu°$, and even $1\mu°$, can be detected.

These and other objects, features and advantages of the present invention will become apparent from the following description when taken in connection with the accompanying drawings, which show, for purposes of illustration only, several embodiments in accordance with the present invention.

BEST MODE FOR CARRYING OUT THE INVENTION

Figure 1:
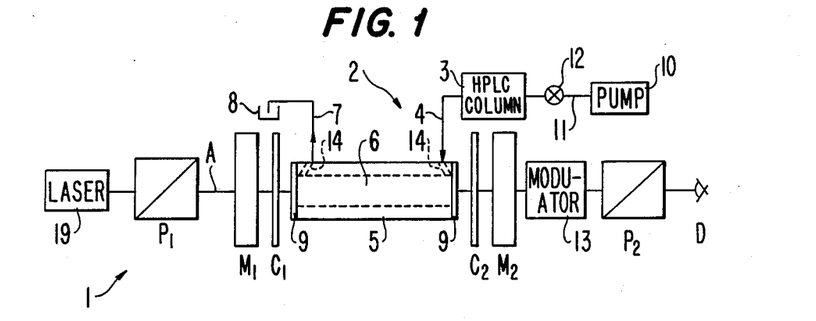
FIG. 1 is a schematic illustration of an optical amplifier for amplifying optical polarization state change effects according to the present invention, the amplifier being shown in use in a high performance liquid chromatography system.

Referring now to the drawings, an optical amplifier 1 for amplifying optical polarization state change effects according to the present invention is illustrated in FIG. 1. The amplifier 1 is an optical rotation parametric amplifier (ORPA) which is used in a high performance liquid chromatography (HPLC) system 2 for detecting and analyzing optically active organic molecules in an eluent flow from the HPLC system 2.

The liquid eluent from the HPLC column 3 of the system 2 flows by way of a passage 4 to a flow cell 5. The eluent enters the cell 5 through an inlet passage 14 and flows through the central bore 6 of the flow cell 5 before exiting the flow cell via outlet passage 14. The eluent leaving the cell is conveyed to a sump 8 via a passage 7. Such a flow cell is shown in U.S. Pat. No. 4,498,774, for example. The ends of the bore 6 of the flow cell 5 are closed against loss of the liquid eluent by optically transparent windows 9 which may, for example, be flat microscope cover slips which will allow transmission of a polarized laser beam without materially affecting the operation of the optical amplifier. Fluid pressure for pumping the eluent from the column 3 through the flow cell 5 to the sump 8 is provided by a pump 10 which is in fluid communication with the column 3 via passage 11 and valve 12.

Figure 13:
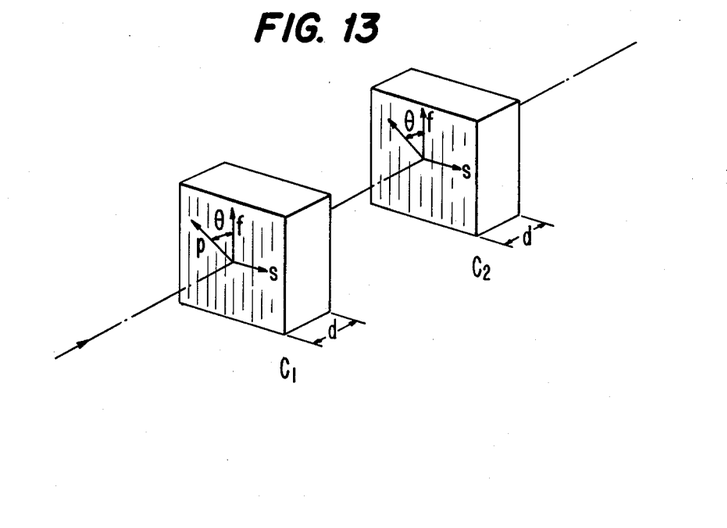
FIG. 13 is a schematic illustration of the two quarter wave compensators of the optical amplifier of the invention located along the optic axis of the amplifier with their neutral lines oriented at the same angle with respect to a direction of polarization P of the incoming light.

The optical amplifier 1 for amplifying optical polarization state change effects which may occur when polarized light is passed through the eluent in the bore 6 of the flow cell 5 comprises a polarizer $P_1$ for polarizing light from a light source 19. The light source 19 is a laser in the illustrated embodiment. The laser directs light along an optic axis A of the amplifier in the direction of the polarizer $P_1$. Light from the laser 19 which is transmitted through the polarizer $P_1$ along the optic axis A is linearly polarized. As shown in FIG. 13, the electric field of the light points in a single direction P in a plane perpendicular to the direction of propagation along optic axis A after having passed through the polarizer $P_1$.

Polarized light propagating in the direction of the optic axis A passes through the material or sample under investigation, in this case the eluent in the central bore 6 of the flow cell 5. If the eluent contains optically active molecules, the direction of polarization P will be rotated in the plane perpendicular to the direction of propagation of the polarized light. Where the concentration of the optically active molecules is very low, the change in the polarization state, that is the amount of the rotation of the polarization direction, is very small so that it is difficult to detect with an analyzer $P_2$ and a detector D as shown in FIG. 1 even with the use of a modulator 13. To avoid this difficulty of detecting weakly optically active materials, according to the present invention, the optical amplifier of the invention takes advantage of the fact that the optical rotation of the polarization direction of the polarized light is directly proportional to the path length of the light traveling through the sample of the material being analyzed. That is, according to the method for detecting optical polarization state change effects according to the invention, and in the optical amplifier of the invention, the path length of the light through the sample is increased by passing at least a portion of the polarized light through the material being analyzed a plurality of times such that changes in the polarization state of the polarized light from the respective passes of the light through the material are cumulative and thus more easily detectable.

For this purpose, the optical amplifier 1 in FIG. 1 is provided with mirrors $M_1$ and $M_2$ located along the optic axis A in opposed relationship at respective, opposite ends of the flow cell 5. The mirrors, when they have a reflectivity R greater than zero, reflect at least a portion of the polarized light back and forth between the mirrors a plurality of times along the optic axis A which extends through the material in the bore 6 of the flow cell 5. The optical polariztion state change effects, in this case, the optical rotations of the polarization direction, from the respective passes of the polarized light through an optically active material would normally cancel each other if the polarized light were simply reflected back and forth between opposing mirrors. In order that the changes in the polarization state of the polarized light from the respective passes of the light through the material are cumulative, according to the method and optical amplifier for amplifying optical polarization state change effects of the invention, the step of passing polarized light through the material further comprises inverting the polarization state of the polarized light between passes through the material so that the changes in the polarization state and successive passes are cumulative.

The inversion of the polarization state is accomplished in the optical amplifier 1 using a pair of quarter wave compensators $C_1$ and $C_2$ which are provided in spaced relationship on the optic axis on opposite sides of the material being analyzed between the material and the means for reflecting. As shown in FIG. 1, the quarter wave compensators $C_1$ and $C_2$ are positioned between the flow cell 5 and the mirrors $M_1$ and $M_2$ at the respective ends of the flow cell. It can be shown through a Jones analysis that the optical rotations from the respective passes will be cumulative, that is, will be added to one another as a result of the half wave retarding effect from the polarized light passing through a quarter wave compensator twice, namely as the polarized light moves toward the adjacent mirror and as it is reflected therefrom back toward the flow cell.

The gain of the optical amplifier of the present invention and the importance of the reflectivity of the mirrors for achieving the amplifier gain are explained below with reference to FIG. 2 of the drawings wherein the mirrors $M_1$ and $M_2$ of the amplifier are shown spaced a distance 1 apart to form a Fabrey-Perot cavity in the amplifier. The mirrors $M_1$ and $M_2$ are interferometer grade mirrors, each having a reflectance (R) and a transmittance (T). The area between them is assumed to be filled with a medium which has an optical rotation of $\alpha$ (degrees/cm). The quarter wave compensators $C_1$ and $C_2$ are necessarily present, although not illustrated in FIG. 2 for simplicity, in order that the optical rotations of the light's polarization direction with the respective passes through the material between the mirrors be cumulative.

Figure 2:
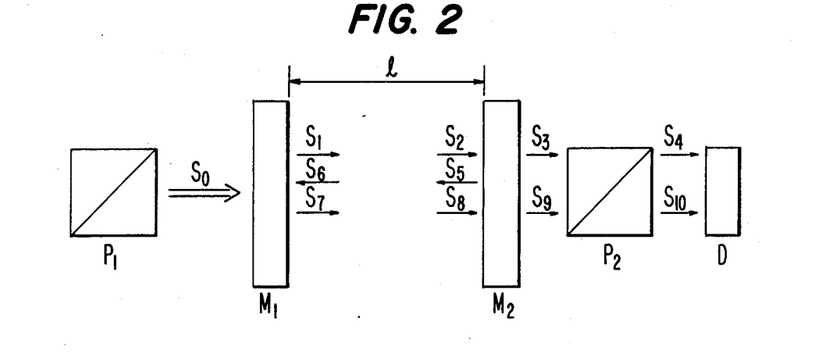
FIG. 2 is a schematic illustration depicting paths of the polarized light in the optical amplifier of FIG. 1, where no modulation takes place and the quarter wave compensators not being shown.

Collimated monochromatic light $S_0$ which has passed through the polarizer $P_1$ is incident upon the mirror $M_1$ during operation of the amplifier 1, as depicted in FIG. 2. The light has a Stokes vector $S_0$ which represents plane polarized light with an azimuth of 0°. $S_0$ is given by:

$$S_0 = \begin{bmatrix} I_0 \\ I_0 \\ 0 \\ 0 \end{bmatrix} \quad (1)$$

where $I_0$ is the initial intensity of the plane polarized light incident upon the mirror $M_1$ from the polarizer $P_1$.

The amount transmitter through the mirror is equal to $TI_0$, so the Stokes vector of the light entering the active medium is:

$$S_1 = \begin{bmatrix} TI_0 \\ TI_0 \\ 0 \\ 0 \end{bmatrix} \quad (2)$$

After traversing the cavity, the plane of polarization has been rotated by $\alpha 1$, so the Stokes vector reaching the mirror $M_2$ is given by:

$$S_2 = R(\alpha 1) S_1 \text{ (where } R \text{ is the rotation matrix)} \quad (3)$$

or;

$$S_2 = \begin{bmatrix} 1 & 0 & 0 & 0 \\ 0 & \cos 2\alpha 1 & \sin 2\alpha 1 & 0 \\ 0 & -\sin 2\alpha 1 & \cos 2\alpha 1 & 0 \\ 0 & 0 & 0 & 1 \end{bmatrix} \begin{bmatrix} TI_0 \\ TI_0 \\ 0 \\ 0 \end{bmatrix} = \begin{bmatrix} TI_0 \\ TI_0 \ (\cos 2\alpha 1) \\ -TI_0 \ (\sin 2\alpha 1) \\ 0 \end{bmatrix} \quad (4)$$

Of $S_2$, an amount is passed through $M_2$ to yield $S_3$ which is described by:

$$S_3 = \begin{bmatrix} T^2 I_0 \\ T^2 I_0 \cos 2\alpha 1 \\ -T^2 I_0 \sin 2\alpha 1 \\ 0 \end{bmatrix} \quad (5)$$

This is passed through the polarizer $P_2$, a Glan-Thompson prism oriented at $P=90°$, which yields $S_4$, which is described by:

$$S_4 = M_{P2} S_3 \text{ or:}$$

$$S_4 = \begin{bmatrix} 1 & -1 & 0 & 0 \\ -1 & 1 & 0 & 0 \\ 0 & 0 & 0 & 0 \\ 0 & 0 & 0 & 0 \end{bmatrix} \begin{bmatrix} T^2 I_0 \\ T^2 I_0 \cos 2\alpha 1 \\ -T^2 I_0 \sin 2\alpha 1 \\ 0 \end{bmatrix} = \begin{bmatrix} T^2 I_0 - T^2 I_0 \cos 2\alpha 1 \\ -T^2 I_0 + T^2 I_0 \cos 2\alpha 1 \\ 0 \\ 0 \end{bmatrix} \quad (6)$$

which will contribute an intensity of:

$$I_{D1} = T^2 I_0 - T^2 I_0 \cos 2\alpha 1 \quad (7)$$

The remainder of $S_2$ is reflected back into the cavity with a Stokes vector given by:

$$S_5 = RS_2 \quad (8)$$

or:

$$S_5 = \begin{bmatrix} RTI_0 \\ RTI_0 \cos 2\alpha 1 \\ -RTI_0 \sin 2\alpha 1 \\ 0 \end{bmatrix} \quad (9)$$

$S_5$ propagates through the active medium and arrives at $M_1$ with a Stokes vector of $S_6$, given by:

$$S_6 = R(\alpha 1)S_5 \text{ or:}$$

$$S_6 = \begin{bmatrix} 1 & 0 & 0 & 0 \\ 0 & \cos 2\alpha 1 & \sin 2\alpha 1 & 0 \\ 0 & -\sin 2\alpha 1 & \cos 2\alpha 1 & 0 \\ 0 & 0 & 0 & 1 \end{bmatrix} \begin{bmatrix} RTI_0 \\ RTI_0 \cos 2\alpha 1 \\ -RTI_0 \sin 2\alpha 1 \\ 0 \end{bmatrix} = \begin{bmatrix} RTI_0 \\ RTI_0 \cos 4\alpha 1 \\ -RTI_0 \sin 4\alpha 1 \\ 0 \end{bmatrix} \quad (10)$$

$S_6$ is partially reflected and partially transmitted at $M_1$. The transmitted portion is disregarded in this analysis since it is either lost entirely, or reflected back onto the source, adding to $I_0$. The reflected beam is described by:

$$S_7 = RS_6 \text{ or:}$$

$$S_7 = \begin{bmatrix} R^2 TI_0 \\ R^2 TI_0 \cos 4\alpha 1 \\ -R^2 TI_0 \sin 4\alpha 1 \\ 0 \end{bmatrix} \quad (11)$$

$S_7$ is then propagated back through the optically active medium to yield:

$$S_8 = R(\alpha 1) S_7 = \begin{bmatrix} R^2 TI_0 \\ R^2 TI_0 \cos 6\alpha 1 \\ -R^2 TI_0 \sin 6\alpha 1 \\ 0 \end{bmatrix} \quad (12)$$

At $M_2$, $S_8$ is partially transmitted yielding $S_9$, which is described by:

$$S_9 = TS_8 = \begin{bmatrix} R^2 T^2 I_0 \\ R^2 T^2 I_0 \cos 6\alpha 1 \\ -R^2 T^2 I_0 \sin 6\alpha 1 \\ 0 \end{bmatrix} \quad (13)$$

which on passing through $P_2$ yields $S_{10}$, given by:

$$S_{10} = M_{p2} S_9 = \begin{bmatrix} 1 & -1 & 0 & 0 \\ -1 & 1 & 0 & 0 \\ 0 & 0 & 0 & 0 \\ 0 & 0 & 0 & 0 \end{bmatrix} \begin{bmatrix} R^2 T^2 I_0 \\ R^2 T^2 I_0 \cos 6\alpha 1 \\ -R^2 T^2 I_0 \sin 6\alpha 1 \\ 0 \end{bmatrix} = \begin{bmatrix} R^2 T^2 I_0 - R^2 T^2 I_0 \cos 6\alpha 1 \\ -R^2 T^2 I_0 + R^2 T^2 I_0 \cos 6\alpha 1 \\ 0 \\ 0 \end{bmatrix} \quad (14)$$

This contributes an intensity at the detector D of:

$$I_{D2} = R^2 T^2 I_0 - R^2 T^2 I_0 \cos 6\alpha 1 \quad (15)$$

The process of reflection is continued so that the intensity at the detector D can be expressed as a sum of the infinite series given by:

$$I_D = \sum_{i=1}^{\infty} I_{Di} = \sum_{i=1}^{\infty} T^2 I_0 R^{2(i-1)} (1 - \cos[(4i - 2)\alpha 1]) \quad (16)$$

or:

$$I_D = T^2 I_0 \sum_{i=1}^{\infty} R^{2(i-1)} (1 - \cos[(4i - 2)\alpha 1]) \quad (17\text{-}1)$$

or, when $\alpha 1 << 1$ in which case $\sin[(2n+1)\alpha 1] = (2n+1)\alpha 1$, and setting $n = i - 1$, $$I_D = 2T^2 I_0 \sum_{n=0}^{\infty} R^{2n} (2n + 1)^2 (\alpha 1)^2 \quad (17\text{-}2)$$

In comparison, if the mirrors, M1 and M2, as well as the quarterwave plates were not present and, therefore, no amplification was possible, the intensity at the detector would be $$I_D = 2I_0 (\alpha 1)^2 \quad (17\text{-}3)$$

Comparing equations 17-2 and 17-3 shows that the optical amplifier in the incoherent case enhances the intensity $I_D$ reaching the detector by the factor $G_I$ where $$G_I = T^2 \sum_{n=0}^{\infty} R^{2n} (2n + 1)^2 \quad (17\text{-}4)$$

Using equation 17-4, the coherent case gain factor $G_I$ can be calculated in terms of the reflectivity, R, of mirrors $M_I$ and $M_2$. For this purpose, R and T are assumed to be related by $R = 1 - T$, that is absorption is neglected, but this would only show up as an apparent slight decrease in T. The gain factor $G_I$ was evaluated for R values of 0.9, 0.99, and 0.999. They are approximately 10, 100, and 1,000, respectively.

The rotational gain possible with the optical amplifier is apparent from these calculations. It is also clear from the results that the reflectivity of the mirrors has a significant effect on the gain. These results and the above analysis are for the incoherent case where the length l between the mirrors in the amplifier is such that a resonant condition does not exist. The amplifier gain, and thus the intensity seen at the detector for a given optical rotation, can be further increased if the length l is adjusted to obtain a resonant or coherent light condition as discussed below.

In the analysis of the coherent case and the resonance condition one must consider the electric field strength of the light in the preferred direction of P1, namely 0°, and P2, namely, 90°, as opposed to the intensity of the light beam used in the incoherent analysis. The electric field of the light after passage through M2 in FIG. 1 is $$^0E = tt(\cos(a) + r^2 e^{id} \cos(3a) + r^4 e^{i2d} \cos(5a) + \ldots) E_0 \quad (17a)$$

and $$^{90}E = tt(\sin)a) + r^2 e^{id} \sin(3a) + r^4 e^{i2d} \sin(5a) + \ldots) E_0 \quad (17b)$$

where: $a = \alpha 1$, $i = \sqrt{-1}$, $d/2$ = phase delay due to a single passage of the light between M1 and M2, $E_0$ is the electric field of the light incident on M1 in the preferred direction of polarizer $P_1$, $°E$ is the electric field in the preferred direction of P1 that is incident on polarizer $P_2$, $^{90}E$ is the electric field in the preferred direction of P2 that is incident on polarizer $P_2$, t is the amplitude transmission coefficient of M1 or M2, r is the amplitude reflectivity of M1 or M2, $R=r^2$, and $T=t^2$. In addition, $R=1-T$ which means that losses in M1 and M2 are neglected. This assumption does not materially affect operation of the optical activity amplifier since interferometer grade mirrors do not have significant losses at the light wavelengths of interest. Realizing that P2 only passes light with electric field parallel to its preferred direction and rejects light with electric field perpendicular to that direction only light described in equation (17b) reaches the detector and needs to be analyzed further.

The amplifier will be in a resonance condition 0 whenever the cavity length is adjusted such that d is an integer multiple of $2\pi$, in which case $e^{ind}=1(n=0,1,...)$ and equation (17b) becomes $$^{90}E = T\{\sin(a) + R\sin(3a) + R^2\sin(5a) + ... + \quad (17c)$$
$$R^n\sin([2n + 1]a)\}E_0,$$

or $$^{90}E = TE_0 \sum_{n=0}^{\infty} R^n \sin[(2n + 1)a] \quad (17d)$$

For weak optical activities, a is small and $\sin[2n+1]a$ is approximated by $[2n+1]a$. Therefore $$^{90}E = aTE_0\{(1+R)/(1-R)^2\} = aE_0(1+R)/T. \quad (17e)$$

The intensity of light reaching the detector is obtained by squaring the right hand portion of equation (17e)

$$I_D = a^2 I_0 (1+R)^2/T^2 \quad (17f)$$

In the case where the optical amplifier is not present and only P1, P2, and the optically active medium are present, the intensity reaching the detector is simply $a^2 I_0$. Thus the factor $(1+R)^2/T^2$ represents the gain achieved by the optical amplifier operated in the resonance condition. For mirror reflectivities, R, of 0.9, 0.99, and 0.0999 the gain is 361, 39,601, and 3,996,001, respectively. This means that if the sensitivity limit of a polarimeter apparatus without an optical amplifier of the invention were 0.001°, the limit of sensitivity with the optical amplifier and 0.99 reflectivity mirrors at resonance condition is $2.5 \times 10^{-8}$ degrees or about 400 times more than using the optical amplifier of the invention in nonresonance condition.

Figure 3:
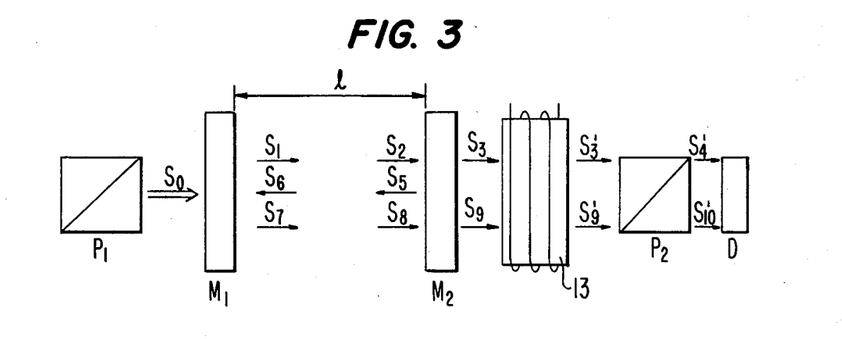
FIG. 3 is a schematic illustration of the optical amplifier of FIG. 1 showing paths of polarized light through the amplifier with an operable modulator, and wherein the quarter wave compensators of the amplifier are not shown.
Figure 4:
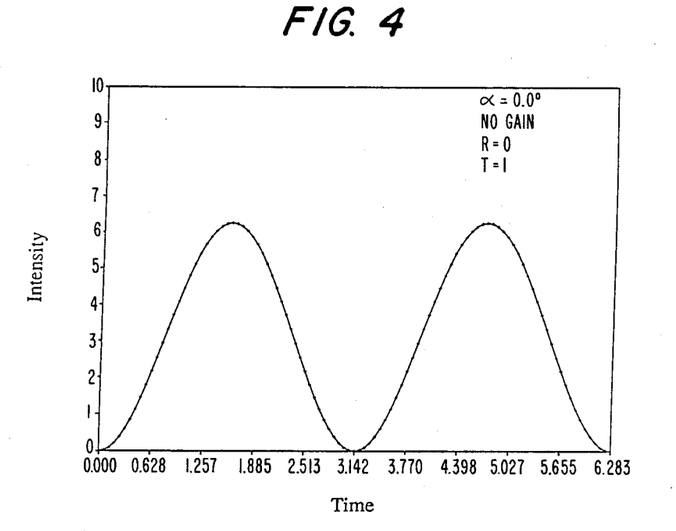
FIGS. 4–12 show the wave forms of the signal at the detector of the optical amplifier of FIGS. 1 and 3 for various values of optical rotation of the polarization direction by a material located between the respective mirrors and quarter wave compensators of the amplifier, in both the no-gain case where the reflectance R of the mirrors is zero and the transmittance T is one, and the case where R=0.99 and T=0.01.
Figure 5:
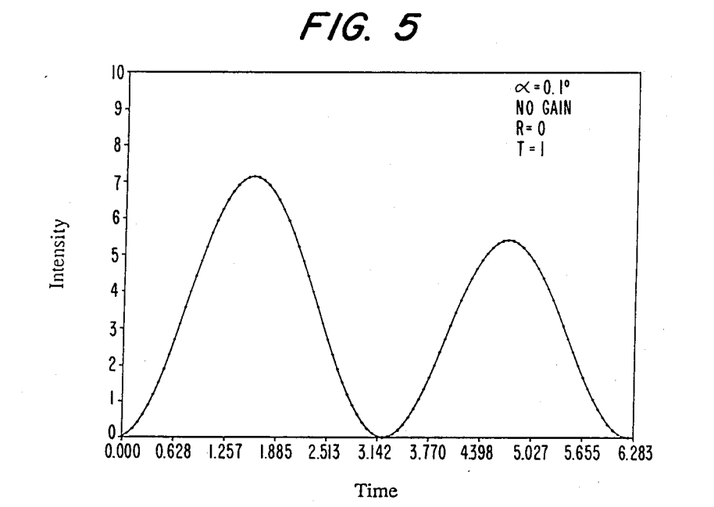
Figure 6:
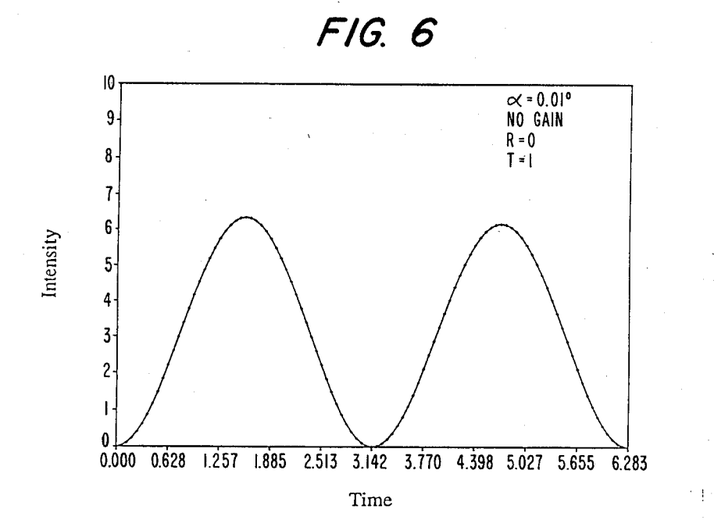
Figure 7:
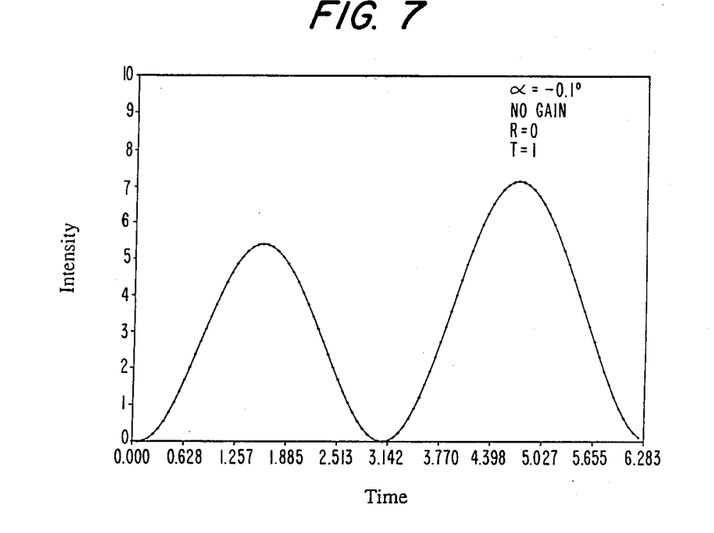
Figure 8:
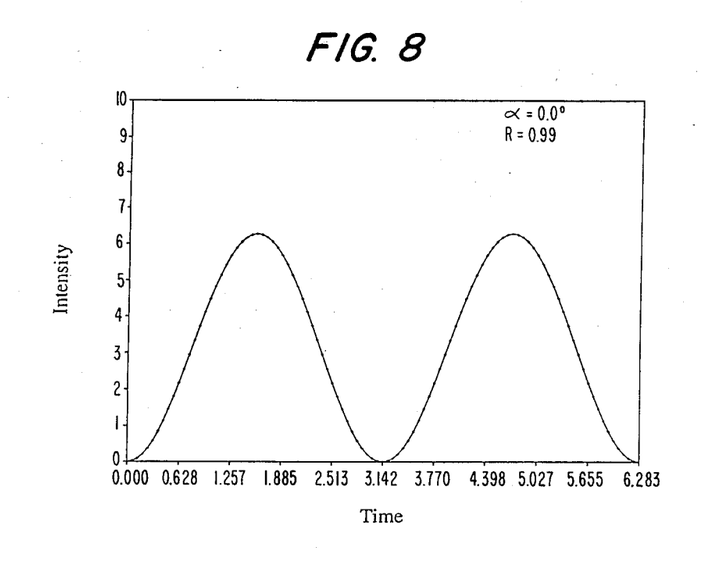
Figure 9:
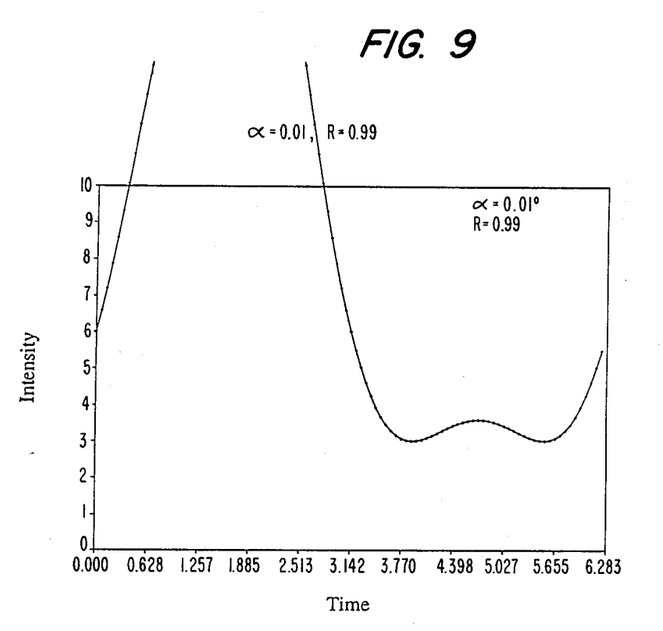
Figure 10:
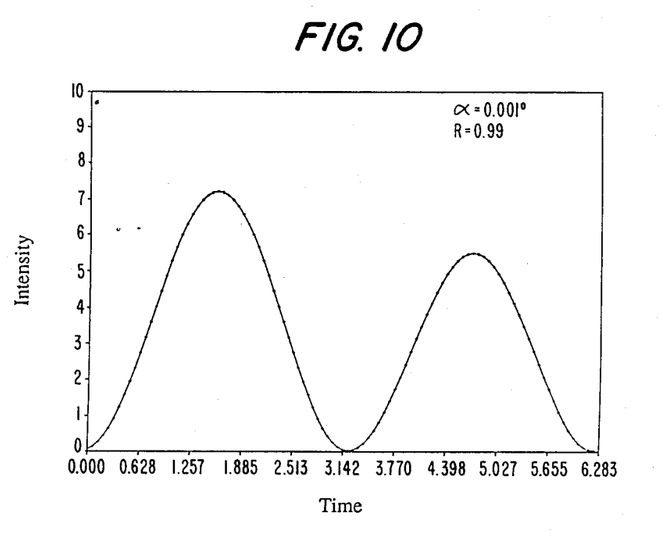
Figure 11:
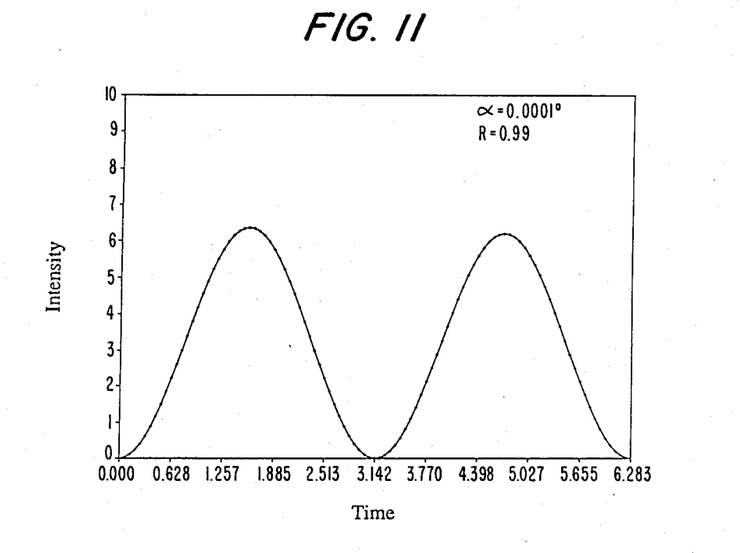
Figure 12:
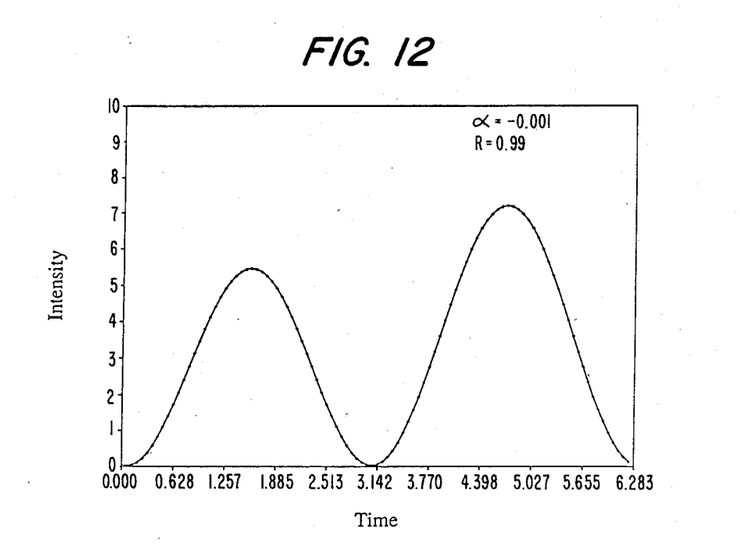

The analysis of the gain of the amplifier of the present invention as discussed above with respect to FIG. 2 assumed no modulation. The case where a modulator such as modulator 13 illustrated in the optical amplifier 1 in FIG. 1 is employed is discussed with respect to FIG. 3, for the incoherent case. The optical amplifier of FIG. 3 is like that of FIG. 2, with the quarter wave compensators not being shown again, but with a modulator 13, which is a Farday modulator being operated during the operation of the amplifier. The above analysis with respect to FIG. 2 applies for FIG. 3 up to equation 5. At this point $S_3$ is passed through the modulator 13, generating $S_3'$, which is described by:

$$S_3' = R(2\pi kwt) S_3 \quad (18)$$

where $R(2\pi k\omega t)$ is the rotation matrix, k is the modulation magnitude (radians), $\omega$ is the modulation frequency, and t is time in seconds. This expands to:

$$S_3 = \quad (19)$$

$$\begin{bmatrix} 1 & 0 & 0 & 0 \\ 0 & \cos(\sin 2\pi\, kwt) & \sin(\sin 2\pi\, kwt) & 0 \\ 0 & -\sin(\sin 2\pi\, kwt) & \cos(\sin 2\pi\, kwt) & 0 \\ 0 & 0^1 & 0 & 1 \end{bmatrix} \begin{bmatrix} T^2 I_0 \\ T^2 I_0 \cos 2\alpha 1 \\ -T^2 I_0 \sin 2\,\alpha 1 \\ 0 \end{bmatrix} =$$

$$\begin{bmatrix} T^2 I_0 \\ \cos(2\alpha 1 + \sin(2\pi kwt)) \\ -\sin(2\alpha 1 + \sin(2\pi kwt)) \\ 0 \end{bmatrix}$$

Upon passing through P2, $S_4'$ is generated, having the form:

$$S_4' = M_{p2} S_3' \quad (20)$$

or $$S_4' = \begin{bmatrix} 1 & -1 & 0 & 0 \\ -1 & 1 & 0 & 0 \\ 0 & 0 & 0 & 0 \\ 0 & 0 & 0 & 0 \end{bmatrix} \begin{bmatrix} T_2 I_0 \\ \cos(2\alpha 1 + \sin(2\pi kwt)) \\ -\sin(2\alpha 1 + \sin(2\pi kwt)) \\ 0 \end{bmatrix} = \quad (21)$$

$$\begin{bmatrix} T_4^2 I_0 - T_2^2 I_0 \cos(2\alpha 1 + \sin 2\pi kwt) \\ -T^2 I_0 - T^2 I_0 \cos(2\alpha 1 + \sin 2\pi kwt) \\ 0 \\ 0 \end{bmatrix}$$

which contributes an intensity at the detector of:

$$I_{D1} = T^2 I_0 - T^2 I_0 \cos(2\alpha 1 + \sin 2\pi kwt) \quad (22)$$

As above, the total intensity at the detector will be given by a series, in this case:

$$I_D = \sum_{i=1}^{\infty} I_{Di} = \quad (23)$$

$$\sum_{i=1}^{\infty} R^{2(i-1)} T^2 I_0 [1 - \cos\{(4i - 2)\alpha 1 + \sin 2\pi kwt\}]$$

which can be expanded to yield:

$$I_D = \quad (24)$$

$$\sum_{i=1}^{\infty} R^{2(i-1)} T^2 I_0 [1 - \cos\{(4i - 2)\alpha 1\}\cos(\sin 2\pi kwt) +$$

$$\sin\{(4i - 2)\alpha 1\}\sin(\sin 2\pi kwt)]$$

In this case, the signal at the detector D will be a complex AC wave form. FIGS. 4–12 show the wave forms for various values of rotation in both the no-gain case $R=0$, $T=1$ and the case where $R=0.99$ and $T=0.01$. From these results, it can be readily seen that the cavity of the optical amplifier has a rotation gain of around 100. Using known digital signal processing, or analog circuitry, rotations of $10\mu°$ and even $1\mu°$ can be measured even in the incoherent case where the reflectivity R is equal to or greater than 0.99.

The above-discussed capabilities of the optical amplifier to detect very small optical rotations assumed the light from the amplifiers was incoherent light. However, if the length l between the mirrors $M_1$ and $M_2$ in the optical amplifier is selected so that a resonance condition of the light exists within the amplifier, the gain and hence, the intensity of the output of the amplifier to the detector can be substantially increased. This permits increased sensitivity for the detection of small amounts of optical rotation. To obtain the resonance condition of the amplifier, known piezoelectric transducers can be provided to adjust the position of the mirrors with respect to one another so as to vary the path length l to obtain the desired constructive interference.

The light source 19 in the optical amplifier 1 of FIG. 1 is a laser. The laser is a preferred light source because it produces a monochromatic light which is very intense. For example, the laser could be a 6328 angstrom helium neon laser of low power. However, other light sources could be used with the amplifier including arc sources with specific easily isolated wavelength bands, tungsten filaments having broad wavelength ranges but with means for isolating the lines with a narrow wavelength, narrow band width interference filter, etc. A bright light source is preferred, regardless of the type of light, since with a high reflectivity mirror $M_1$ only a small percentage of the output of the light source is able to pass through the mirror and before reaching the mirror $M_1$, light from the source 19 is halved by the polarizer $P_1$.

The polarizer $P_1$ receives the unpolarized light from the laser 19 and transmits only linear polarized light along the optic axis A in the direction of the mirror $M_1$. Preferably, the polarizer $P_1$ is a high quality birefringent crystal polarizer such as a Glan-Thompson polarizer formed of a crystal material such as calcite, quartz, magnesium fluoride or other suitable birefringent material. Alternatively, other types of polarizers could be employed such as a dichroic polarizer.

The analyzer $P_2$ in the optical amplifier 1 disclosed in FIG. 1 is a polarizer like $P_1$, that is, a Glan-Thompson polarizer. Both polarizers $P_1$ and $P_2$ are preferably of highest quality with, for example, an extinction ratio, the rate at which it rejects one polarization and transmits another, being as high as a million times or $10^6$. The polarizers $P_1$ and $P_2$ are used cooperatively to analyze the direction of the linearly polarized light transmitted through the amplifier. The optical rotation amplifier 1, thus, is a polarimeter amplifier. Where, for example, the preferred directions of the polarizers $P_1$ and $P_2$ are crossed at 90° in the plane perpendicular to the optic axis A, and the material between the mirrors $M_1$ and $M_2$ is not optically active, no polarized light passes through the analyzer $P_2$ to the detector D. However, where the polarized light passes through an optically active material such as the eluent in the flow cell 5, the direction of polarization is rotated and light will be transmitted through the polarizer $P_2$ to the detector in an amount corresponding to the angle of rotation.

The equation governing the intensity $I_D$ that the detector D sees is: $I_D = I_0 \cos \Theta$ where $I_0$ is the incident intensity upon the polarizer $P_2$ and the angle $\Theta$ is the angle between the preferred direction of the polarizer and the actual polarization direction of the light. When $\Theta$ is zero cos is 1, so there is maximum transmission and when $\Theta$ is 90°, cos is zero and there is nothing transmitted. Both polarizers $P_1$ and $P_2$ are located in a plane perpendicular to the optic axis A. The optical amplifier 1 of the invention acts to amplify the effect of small rotations to permit their detection using the analyzer $P_2$ rotationally fixed in position and measuring the intensity at the detector D.

The liquid chromatography system 2 shown in FIG. 1 involves the use of a carrier liquid which is flowed through the column 3, passage 4, flow cell 5, passage 7 to the sump 8 as discussed above. The carrier fluid serves as a reference liquid. The output intensity of the amplifier 1 is monitored over time with the detector D. A recorder can be used to plot the output intensity versus time. The recording would show a base line for the output intensity associated with the reference liquid and then an increase or decrease in intensity depending on the direction of rotation caused by the presence of an optically active material in the carrier liquid. This information can be used to identify what the optically active material is and the amounts or concentration thereof as is conventional in this type of chromatography The mirrors $M_1$ and $M_2$ in FIG. 1 are shown as plane mirrors located in a plane perpendicular to the optic axis A so that they allow theoretically an infinite number of reflections of the light back and forth between them, depending upon the reflectivity R of the mirrors. The mirrors form what is called a Fabrey Perot cell or cavity. Instead of plane mirrors, the mirrors could be focusing mirrors of long focal length. They could also have a confocal design.

From the above equations, it can be seen that the intensity at the detector is a function of the mirror reflectivities, that is, the gain of the amplifier is directly proportional to the reflectivity of the mirrors. The reflectivity R of the mirrors is 0.90 or, more preferably at least 0.99 for enhanced amplifier gain. The mirrors can be formed, for example, with a fused silica base with magnesium fluoride overcoated aluminum. Other well known mirror materials could also be used. Piezoelectric transducers, not shown, can be provided on the mirrors to always hold the cavity in tune or resonance condition for high transmission and sensitivity. The transducers also dynamically compensate for temperature changes in the cell 5.

The quarter wave compensators or retarders $C_1$ and $C_2$ of the amplifier 1 are standard polarization devices which can for example, be made out of birefringent material such as calcite, quartz or mica. Each retarder has a fast axis or preferred direction identified by the arrow f in FIG. 13 and a slow axis identified by the arrows s in FIG. 13. Inside of each compensator, light that propagates with the electrical field parallel to the fast axis travels faster than light polarized parallel to the slow axis so that after transmission through the quarter wave compensator, when the two components reemerge they are no longer in phase. The amount of the phase shift depends on the thickness d of the compensator. With the present invention, the gain of the amplifier directly depends upon the precision of the quarter wave compensators in order to get close to theoretical performance for a given set of reflectivities of the mirrors. Accordingly, the retardation of each compensator is preferably as close as a few tenths of a degree from 90° as a retarder, e.g., 90°±0.3°. As discussed above, the effect of the quarter wave compensators is to invert the direction of polarization on reflection, that is, after two passes of the light through the compensator. This causes the optical rotations of the light with respective passes of the light through the material to be cumulative. The axes f and s, also referred to as the neutral lines of the compensators, form the same angles with respect to the direction of polarization P of the polarized light supplied to the polarizer $P_1$.

If no modulation is performed as with the amplifier discussed with reference to FIG. 2, the output of the detector d will merely be a dc change in the intensity with respect to a base line when an optically active material is present in the eluent. With a modulator 13 as shown in FIG. 1, there will be a time varying intensity change that is a function of how the modulator operates. The modulator 13 is preferably a sine or square wave driven Faraday modulator which is placed in the beam outside the Fabrey Perot cavity of the amplifier, although the modulator could be placed inside the cavity. Other types of modulators such as photoelastic modulators could also be used to continuously modulate the polarization state of the light in terms of retardation or phase change and azimuth. The purpose of all of these different types of modulators is to modulate the photoelectric detected intensity in relation to the polarization state changes. Modulation is not necessary with the optical amplifier of the present invention but it makes it easier to detect the polarization state change effects amplified by the amplifier as discussed above. If a modulator is used, such as a Faraday modulator, it will be sensitive to the sign of the rotations, that is, whether positive or negative. If no modulator is used, the sign of the optical rotation of the polarization direction can be detected by a slight angular displacement of the analyzer $P_2$.

The detector D illustrated schematically in FIG. 1 is shown as the human eye but in automated systems the detector is preferably some kind of photosensitive detector, a photomultiplier, photodiode or phototransistor, for example. The detector merely detects the intensity change without the optically active material and with the optically actively material and then knowing other parameters associated with the liquid chromatography system, the optically active material and its concentration can be computed.

The flow cell 5 can be a flow cell of the type disclosed in U.S. Pat. No. 4,498,774, for example. The cell is constructed of fused quartz or some other low expansion optical material which is chemically inert. It has an annular central bore 6 formed therein along the length of the entire cell. The open ends of the central bore 6 are closed by windows 9. The material of the cell itself need not be light transmissive, only the end windows 9 have to be constructed so as to be light transmissive. Instead of a non-metallic material, the cell could also be constructed of a metal which is not reactive to the materials to be used therein, for example, a very low expansion steel such as Invar could be used.

The light transmissive end windows 9 can be formed of fused silica, for example. Microscope cover slips will work as end windows, epoxied to the cell material, if the bore 6 is small enough. Practical lengths for the flow cell 5 are from 1 mm to 200 mm, with typical cells being in the range of 1-100 mm, depending upon the application. The diameter of the bore 6 must necessarily be large enough to avoid interference with the polarized light beam passing through the eluent within the bore 6, but the volume of the cell at a minimum to minimize the necessary amount of material to fill the bore 6 within the cell for analysis. The small passages 14 extending between the periphery of the flow cell and the bore 6 permit the ingress and egress of the eluent under the force of the system pressure.

Figure 14:
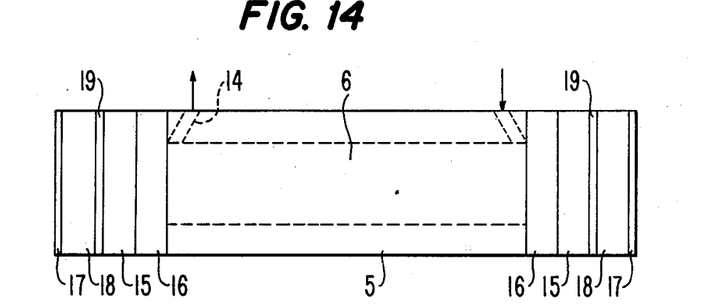
FIG. 14 is a schematic illustration of a flow cell of the invention which is formed integrally with optical elements of the amplifier.

In the embodiment of the invention illustrated in FIG. 1, the several components of the amplifier are individually fixed with respect to one another along the optic axis A as by mechanical clamping. Alternatively, one or more of the mirrors, compensators and polarizers can be formed integrally with the flow cell. As shown in FIG. 14, each end of the flow cell 5 includes a quarter wave plate 15 of crystalline quartz or mica, for example. If mica, the quarter wave plate is covered with a plate 16 of fused silica, glass or other suitable optical media for the wavelength of interest to protect the mica. The end of the flow cell 5 is bonded using an adhesive epoxy, for example, to the cover plate 16 to close the end of the bore 6. Alternatively, the cover plate 16 could be sealed to the end of the flow cell 5 with O-rings or gaskets and clamped in place. It also could be sealed without a sealer of any kind under the application of light pressure to form a leak proof seal if the end of the cell and the adjacent cover plate are highly polished optically flat.

In this embodiment, the polarizers 17 are in the form of a dichroic polarization coating on a fused silica, glass or other suitable optical media, substrate 18. The face of the substrate 18 opposite that carrying the polarizer 17 is coated with a reflective coating 19 as a mirror. For example, a dielectric reflective coating or an aluminum reflective coating could be provided on the substrate 18 to serve as the mirror. The reflective coating is in turn bonded or laminated to the quarter wave plate 15 to form an integral assembly for the amplifier. For temperature stabilization, as an added feature, a cooling device could be provided in the cell 5 to stabilize the temperature of the cell. The temperature of the eluent could also be precooled to correspond to the temperature of the flow cell, so as not to destroy the temperature equilibrium of the cell.

The amplifier of the invention shown in FIG. 1 could also be modified by using a single, two beam polarizer rather than two separate polarizers $P_1$ and $P_2$. The single polarizer would serve as both polarizer and analyzer. The amplifier 1 could also be used to analyze liquids other than eluents from liquid chromatography systems by flowing the liquid to be analyzed through the flow cell 5. In addition, the optical amplifier 1 of the invention can be used to analyze materials other than liquid, for example, gases and solids. The flow cell 5 could be removed from between the mirrors $M_1$ and $M_2$ and replaced by the solid or gas to be analyzed.

Further, the optical amplifier could be used to investigate the magneto optical effect on gases, liquids or solids where the material is contained inside a solenoid or a coil carrying electric current so that whatever material appears inside the coil will, even though normally not optically active, become optically active due to the effect of the magnetic field. Electro-optical polarization effects can also be analyzed by applying electric fields to materials located within the area between the mirrors and quarter wave compensators of the amplifier. The increased sensitivity of detecting optical polarization state change effects according to the invention can also be advantageously used in environmental situations, for example, where to a great degree the concentrations of some quantities to be measured may be as low as several parts per billion. The optical amplifier also has applicability in the detection of small amounts of substance abuse materials that show optical activites, for example, in forensic laboratories for analysis in drug abuse cases. The gain of the amplifier of 100 or more for amplifying optical polarization state change effects, thus permits improved detection and measurement in a wide variety of applications.

Accordingly, while I have shown and described only several embodiments in accordance with the present invention, it is understood that the same is not limited thereto, but is susceptible to numerous changes and modifications as known skilled in the art. Therefore, I do not wish to be limited to the details shown in described herein, but intend to cover all such changes and modifications as are encompassed by the scope of the appended claims.

I claim:

1. An optical amplifier for amplifying optical polarization state change effects comprising means for providing polarized light and means for passing at least a portion of said polarized light through a material a plurality of times such that changes in polarization state of the polarized light from the respective passes of the light through said material are cumulative, wherein said means for passing includes means for reflecting at least a portion of said polarized light back and forth on itself a plurality of times along an optic axis which extends through said material thereby forming an optical cavity, and wherein said means for passing inverts the polarization state of the polarized light between passes through said material so that the changes in the polarization state in successive passes are cumulative.

2. An optical amplifier according to claim 1, wherein said means for inverting includes a pair of quarter wave compensators which are provided in spaced relationship on said optic axis on opposite sides of said material between said material and said means for reflecting.

3. An optical amplifier according to claim 2, wherein the retardation of each quarter wave compensator is 90°±1.0°.

4. An optical amplifier according to claim 2. wherein each quarter wave compensator has two neutral lines, the neutral lines of each quarter wave compensator forming the same angles with respect to a direction of polarization of the polarized light from said means for providing polarized light.

5. An optical amplifier according to claim 1, wherein said means for reflecting includes a pair of mirrors which are provided in spaced relationship on said optic axis on opposite sides of said material for reflecting at least a portion of said polarized light back and forth a plurality of times along said optic axis through said material.

6. An optical amplifier according to claim 5, wherein said mirrors each have a reflectivity R which is at least about 0.9.

7. An optical amplifier according to claim 1, further comprising means for analyzing the polarization state of polarized light passed through said material.

8. An optical amplifier according to claim 7, wherein said means for analyzing polarized light comprises a polarizer.

9. An optical amplifier according to claim 7, further comprising a photosensitive detector for detecting light intensity from said means for analyzing the polarization state of the polarized light passed through said material.

10. An optical amplifier according to claim 7, further comprising means for modulating the polarization state of the light which is received by said analyzing means.

11. An optical amplifier according to claim 1, wherein the length of the path along said optic axis along which polarized light is reflected back and forth is selected to provide a resonance condition.

12. An optical amplifier according to claim 1, further comprising a cell containing said material through which said polarized light is passed.

13. An optical amplifier according to claim 12, wherein said cell is a flow cell which is connected to a column of a high performance liquid chromatography system.

14. An optical amplifier according the claim 12, wherein said means for passing is formed integrally with said cell.

15. An optical amplifier according to claim 12, wherein said means for passing comprises a pair of quarter wave compensators which are attached to respective, opposite ends of said cell.

16. An optical amplifier according to claim 15, wherein said means for passing further comprises a pair of mirrors which are attached to respective ones of said quarter wave compensators.

17. An optical amplifier according to claim 16, wherein said means for passing further comprises polarizer means attached to at least one of said mirrors.

18. In a liquid chromatography system comprising a cell for containing a liquid chromatography sample and an apparatus for analyzing the sample in said cell for optical activity, the improvement comprising said apparatus including an optical amplifier for amplifying optical polarization state change effects, said amplifier including means for providing polarized light and means for passing at least a portion of said polarized light through a sample in said cell a plurality of times such that changes in the polarization state of the polarized light through said material are cumulative, wherein said means for passing includes means for reflecting at least a portion of said polarized light back and forth on itself a plurality of times along an optic axis which extends through said material thereby forming an optical cavity, and wherein said means for passing inverts the polarization state of the polarized light between passes through said material so that the changes in the polarization state in successive passes are cumulative.

19. A method for detecting optical polarization state change effects comprising the steps of providing polarized light, passing at least a portion of the polarized light through a material a plurality of times such that changes in the polarization state of the polarized light from the respective passes of the light through said material are cumulative, and detecting polarized light which has passed through said material, wherein said step of passing polarized light through said material a plurality of times comprises reflecting light back and forth on itself a plurality of times along an optic axis which extends through said material thereby forming an optical cavity and inverting the polarization state of the polarized light between passes through said material so that the changes in the polarization state in successive passes are cumulative.

20. A method according to claim 19, wherein said material is a liquid.

21. A method according to claim 19, wherein said material is a gas.

22. A method according to claim 19, wherein said material is a solid.

23. An optical amplifier for amplifying optical polarization state change effects comprising means for providing polarized light and means for passing at least a portion of said polarized light through a material a plurality of times such that changes in polarization state of the polarized light from the respective passes of the light through said material are cumulative, wherein said means for passing includes means for reflecting at least a portion of said polarized light back and forth on itself a plurality of times along an optic axis which extends through said material thereby forming an optical cavity.

* * * * *